(12) United States Patent
Robinson, Jr.

(10) Patent No.: US 8,408,164 B2
(45) Date of Patent: Apr. 2, 2013

(54) SYSTEM AND METHOD FOR RELEASE AND DISPERSION OF FLIES OR OTHER BIOLOGICAL CONTROL

(76) Inventor: Richard David Robinson, Jr., Fort Pierce, FL (US)

( * ) Notice: Subject to any disclaimer, the term of this patent is extended or adjusted under 35 U.S.C. 154(b) by 30 days.

(21) Appl. No.: 12/876,895

(22) Filed: Sep. 7, 2010

(65) Prior Publication Data
US 2011/0132278 A1    Jun. 9, 2011

Related U.S. Application Data

(60) Provisional application No. 61/240,069, filed on Sep. 4, 2009.

(51) Int. Cl.
*A01K 67/00* (2006.01)
*A01K 29/00* (2006.01)
(52) U.S. Cl. .................. 119/843; 119/6.5; 119/174
(58) Field of Classification Search .............. 119/843, 119/6.5, 174, 30
See application file for complete search history.

(56) References Cited

U.S. PATENT DOCUMENTS

| | | | |
|---|---|---|---|
| 3,468,289 A * | 9/1969 | Broida | 119/6.5 |
| 3,871,330 A * | 3/1975 | Swanson et al. | 119/6.5 |
| 4,572,427 A * | 2/1986 | Selfridge et al. | 236/3 |
| 4,594,964 A * | 6/1986 | Vargas et al. | 119/6.6 |
| 4,765,274 A * | 8/1988 | Pizzol et al. | 119/6.6 |
| 4,850,305 A * | 7/1989 | Georgi et al. | 119/6.6 |
| 5,113,799 A * | 5/1992 | Carr et al. | 119/6.5 |
| 5,178,094 A * | 1/1993 | Carr et al. | 119/6.5 |
| 5,351,643 A * | 10/1994 | Hughes | 119/6.5 |
| 6,244,213 B1 * | 6/2001 | Tedders et al. | 119/6.6 |

* cited by examiner

*Primary Examiner* — Yvonne Abbott
(74) *Attorney, Agent, or Firm* — Greenberg Traurig LLP

(57) ABSTRACT

A system and method of release and dispersion of genetically altered flies or other insects to control insect population. The apparatus can be carried by an aircraft and includes removable fly chambers that contain fly containment cylinders. A refrigeration system operates to physically retard the fruit flies. The flies are then released from the fly containment cylinders and fall to the bottom of the fly chamber. Gates on the bottom of the fly chamber are opened manually or remotely to allow the refrigerated flies to fall through the nesting chute into the spiral release controllers. The spiral release controllers dispense the genetically altered flies into the exit chute. The genetically altered flies travel through the exit chute, fall to the earth below and mate with the population thus serving to decrease population by capitalizing on a weakness in the reproductive cycle of the fruit fly or other insect.

17 Claims, 5 Drawing Sheets

Figure 1:
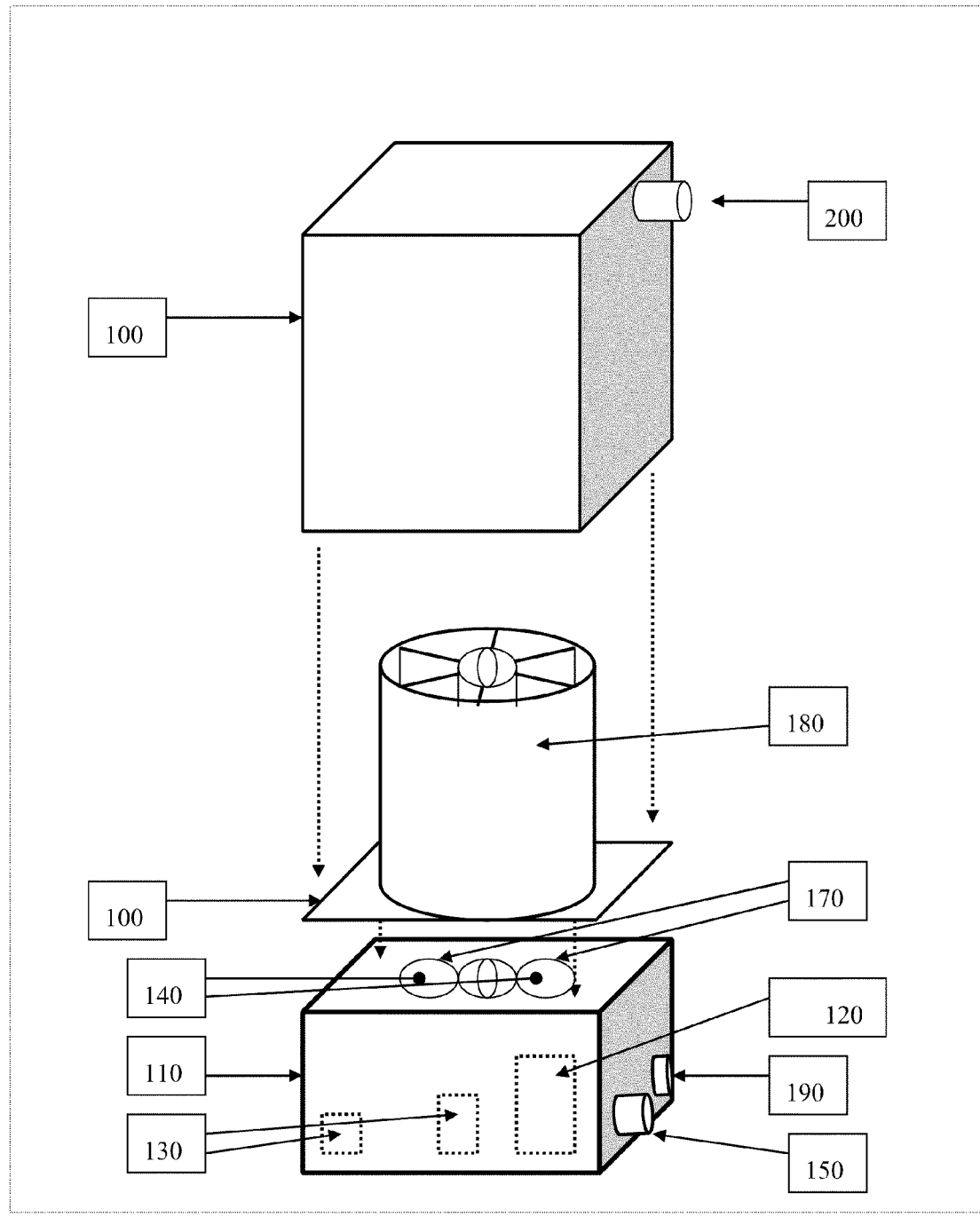
Figure 2:
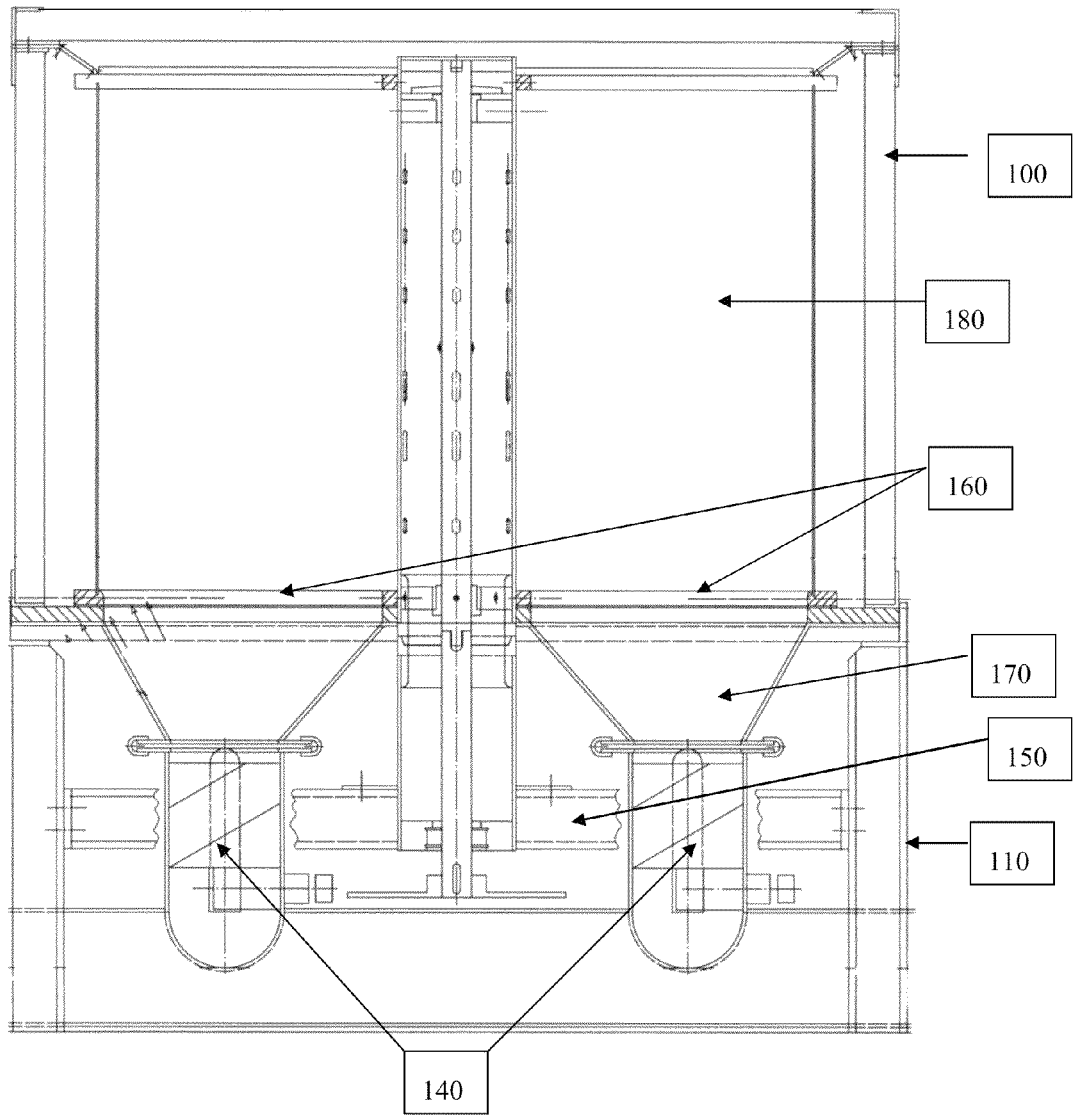

SYSTEM AND METHOD FOR RELEASE AND DISPERSION OF FLIES OR OTHER BIOLOGICAL CONTROL

This application claims priority to U.S. Provisional Patent Application No. 61/240,069 filed Sep. 4, 2009, the entire disclosure of which is incorporated herein by reference. This application includes material which is subject to copyright protection. The copyright owner has no objection to the facsimile reproduction by anyone of the patent disclosure, as it appears in the Patent and Trademark Office files or records, but otherwise reserves all copyright rights whatsoever.

FIELD OF THE INVENTION

In general the field of the invention relates to insect control. Specifically, the field of the invention relates to an apparatus and method for airborne or ground dispersion of genetically altered or sterile flies, other biological insects, or an oral contraceptive to control or eradicate insect populations or wild animal populations such as feral hogs.

BACKGROUND OF THE INVENTION

Insects, and the damage they cause, are a serious economic threat to farmers worldwide. Importing countries, for example, will block fruit and vegetable shipments from certain exporting countries, rather than risk their phytosanitary status by importing foreign fruits, vegetables and other agricultural products.

One insect that is of major concern today is the fruit fly. There are over 4,000 species of fruit flies worldwide. The genus *Anastrepha*, found throughout the Americas, Florida and the Caribbean Islands, comprises approximately 180 species. Of these 180 species, 7 cause serious economic damage.

The Mediterranean Fruit Fly or Medfly (*Ceratitis capatata*), is the most widespread and damaging fruit fly in the world. The Medfly can currently be found in Guatemala and the Mexican states bordering Guatemala. If the Medfly reaches Oaxaca and/or Veracruz, it will have a corridor to the United States. Countermeasures, particularly effective means of pest control, are needed to prevent the spread of the Medfly to the United States. One method of control amounts essentially to birth control.

The female fruit fly has a life-span of 50 days, and will mate only once within her life-span. Thus, dispersing sterile male fruit flies or genetically modified fruit flies that later mate with the female fruit fly breaks the life-cycle of the fruit fly and decreases the population.

SUMMARY OF THE INVENTION

The invention includes a novel apparatus and method which allows for the dispersion of genetically altered flies in a controlled manner to control the population of a given species.

Additional features and advantages of the invention will be set forth in the description which follows, and in part will be apparent from the description, or may be learned by practice of the invention. To achieve these and other advantages and in accordance with the purpose of the present invention, as embodied and broadly described, there is provided an apparatus for utilization with an aircraft that advantageously dispenses genetically altered flies in a controlled and efficient matter in accordance with a method of population control.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention FIG. 1 is an exploded side view of an embodiment of the present invention.

FIG. 2 is a side dissected cross sectional view of the fly chamber and fly containment cylinder seated upon the platform according to the present invention.

FIG. 3 is a top view of the motor drive assembly for the spiral release controllers of the present invention.

FIG. 4 is a top view depicting the refrigeration system of the present invention.

FIG. 5 is a block diagram illustrating the electronic control system in accordance with an embodiment of the invention.

DETAILED DESCRIPTION OF A PREFERRED EMBODIMENT

FIG. 1 illustrates a preferred embodiment of the invention wherein cubical fly chambers 100 are set in a frame 110 that is secured to or contained within an aircraft. The frame 110 of the apparatus sits upon a platform that is secured to the floor of the carrying aircraft. In the preferred embodiment, the base of the frame 110 consists of four sides comprised of aluminum sheeting with support members. The frame 110 houses electrical and control equipment 120, motors 130, the turning spiral release controllers 140 beneath the chutes 170, the fly chambers 100, and the fly containment cylinders 180 within the fly chambers 100. A control box 120 is mounted at the rear of the frame and houses the mechanisms that control the refrigeration system, fly release gates 160 located beneath the base of the fly chamber, and spiral release controllers 140. The looped refrigeration system airflow duct 190 enters through the frame 110 and exits from the fly chamber 200 after circulating through the fly containment cylinder 180 within the fly chamber 100. This multi-compartmented cylinder 180 is constructed with sufficient ventilation access to the central core, perforation of the cylinder compartment dividers, and perforation of the outside cylinder walls to insure adequate movement of cooling air through the entire fly containment cylinder 180 and into the surrounding fly chamber 100 for recapture and return to the cooling facility. Cooling air is fed up through the core of the fly containment cylinder 180, disperses throughout the perforated cylinders to be recaptured at a return air port 200 in the wall of the fly chamber 100

The size of the fly chambers 100 and frame 110 varies according to the dimensions of the aircraft. The number of these units linked together may also vary. One of ordinary skill in the art will readily appreciate that the dimensions of the present invention are dictated by the size of the carrying aircraft and desired fly carrying capacity.

FIG. 2 shows a cross-sectional view through the fly chamber 100 and frame 110. The nesting chutes 170 are designed to support the fly chambers 100 and funnel the sterile or genetically altered flies towards the spiral release controllers 140 which dispense the flies into the exit chute 150. The shape of the nesting chutes 170 can vary, and may be conical or pyramidal but in any embodiment the nesting chutes 170 are shaped to facilitate the funneling of the flies downwards towards one or more spiral release controllers 140. Fly release gates 160 are located in the base of the fly chamber 100 and control discharge from the fly containment cylinders into the nesting chutes 170 and thence to the spiral release controllers.

In a preferred embodiment, the fly chambers 100 are constructed of high-impact foam encased in an aluminum/foam shell. Such a construction presents several advantages, including lightness, sturdiness and insulation capability. The lid of each fly chamber 100 is removable.

Each fly chamber 100 contains a fly containment cylinder 180. Each fly containment cylinder 180 rotates to allow alignment of each individual compartment within the cylinder with the nesting chutes and thence spiral release controllers. Each cylinder is secured to the base of its respective fly chamber 100. Each fly containment cylinder 180, with its multiple compartments contains a number of flies, depending on the amount needed. The bottom of each fly chamber 100 has one or more release gates 160 to release flies from the fly containment cylinder 180 into the nesting chutes 170 and thence the spiral release controllers 140. The gates 160 may be released manually by the operator or by motors which rotate the gates 160 open or closed in the bottom of the fly chamber 100. In an embodiment containing motors to release the fly chamber release gates 160, the motors are controlled by either switches or a CPU housed in the control box 120. In a preferred embodiment in which the carrying aircraft is a Cessna Caravan Airplane, the fly containment cylinders 180 within each respective fly chamber 100 hold approximately 10-15 million flies. The frame 110 holds two fly chambers 100 in the preferred embodiment, however an alternative for use in small aircraft, helicopters or ground vehicle uses only a single fly chamber supported on a smaller frame.

Figure 3:
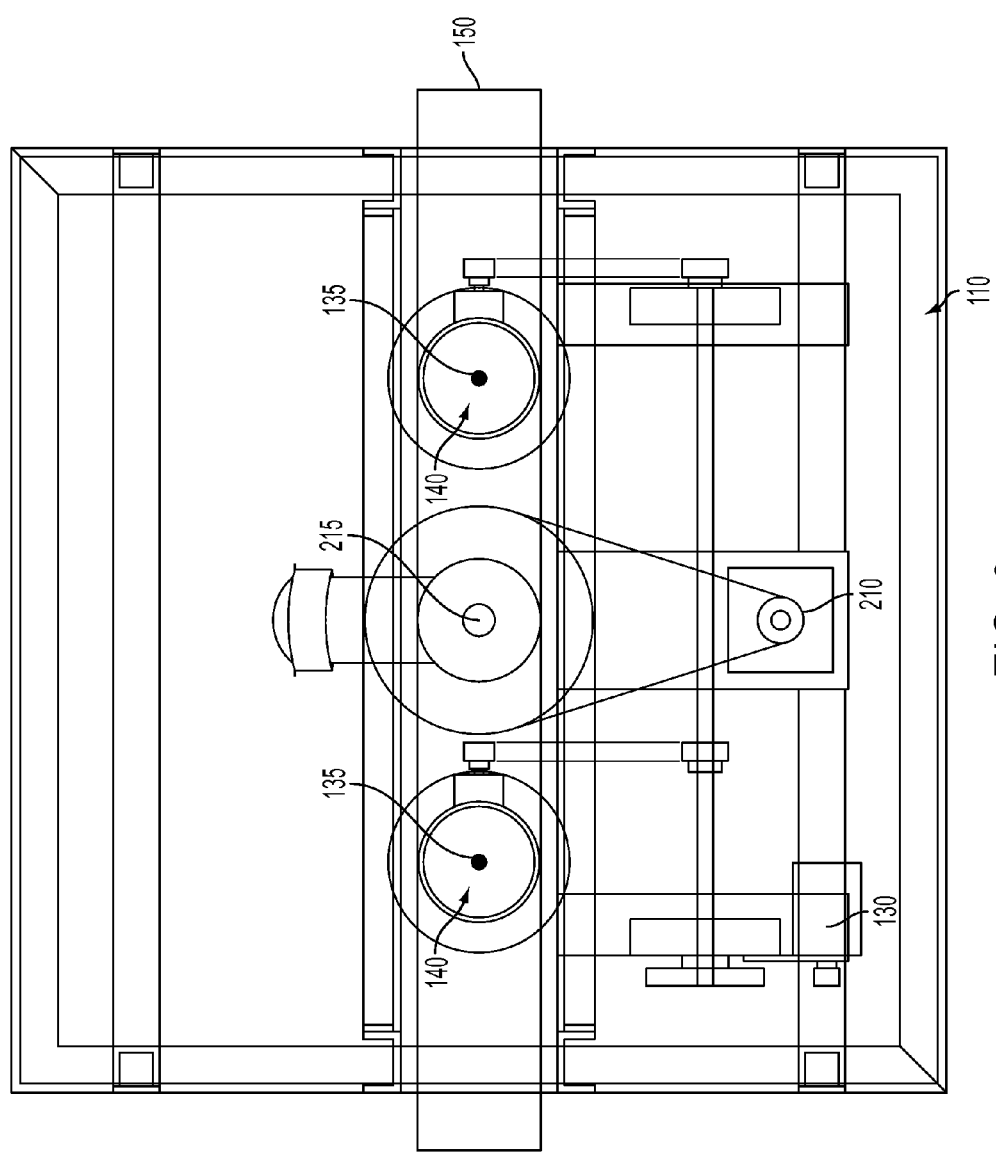

FIG. 3 is a top view of the fly containment cylinder indexing system and the spiral release controllers beneath a fly chamber. The spiral release controllers 140, in a preferred embodiment, are perpendicular with the exit chute 150, which runs horizontally throughout the bottom of the frame and terminates at the exterior of the carrying aircraft. In any embodiment, there is at least one spiral release controller 140 for each fly chamber. In the preferred embodiment shown, there are two spiral release controllers for each fly chamber. These spiral release controllers may be used either simultaneously, or selectively. In the preferred embodiment utilizing two fly chambers, each with its own dedicated spiral release controllers, the controllers may be operated at different rates. This permits this fly release system to drop multiple species simultaneously at different release rates.

FIG. 3 shows a preferred embodiment in which a 24V DC motor 130 turns the spiral release controllers 140 via use of a belt drive. Each spiral release controller 140 rotates upon an axis 135 comprised of a rod of metal, such as stainless steel or aluminum. An indexing motor 210 controls the rotation of the fly containment cylinder shaft 215 and insures precise alignment of fly cylinder compartments over the nesting chutes. The operator, or in the preferred embodiment, the CPU, controls the speed of the rotation of the spiral release controllers 140 and therefore the dispersion rate of the sterile or genetically altered flies.

The fly chamber 100, when seated in the frame 110 abuts the fly chamber 100 next to it, and is ported to allow circulation of refrigerated air among the fly chambers 100. The refrigeration system is separated from the fly release machine frame such that it may be ducted to one or more fly release machines.

Figure 4:
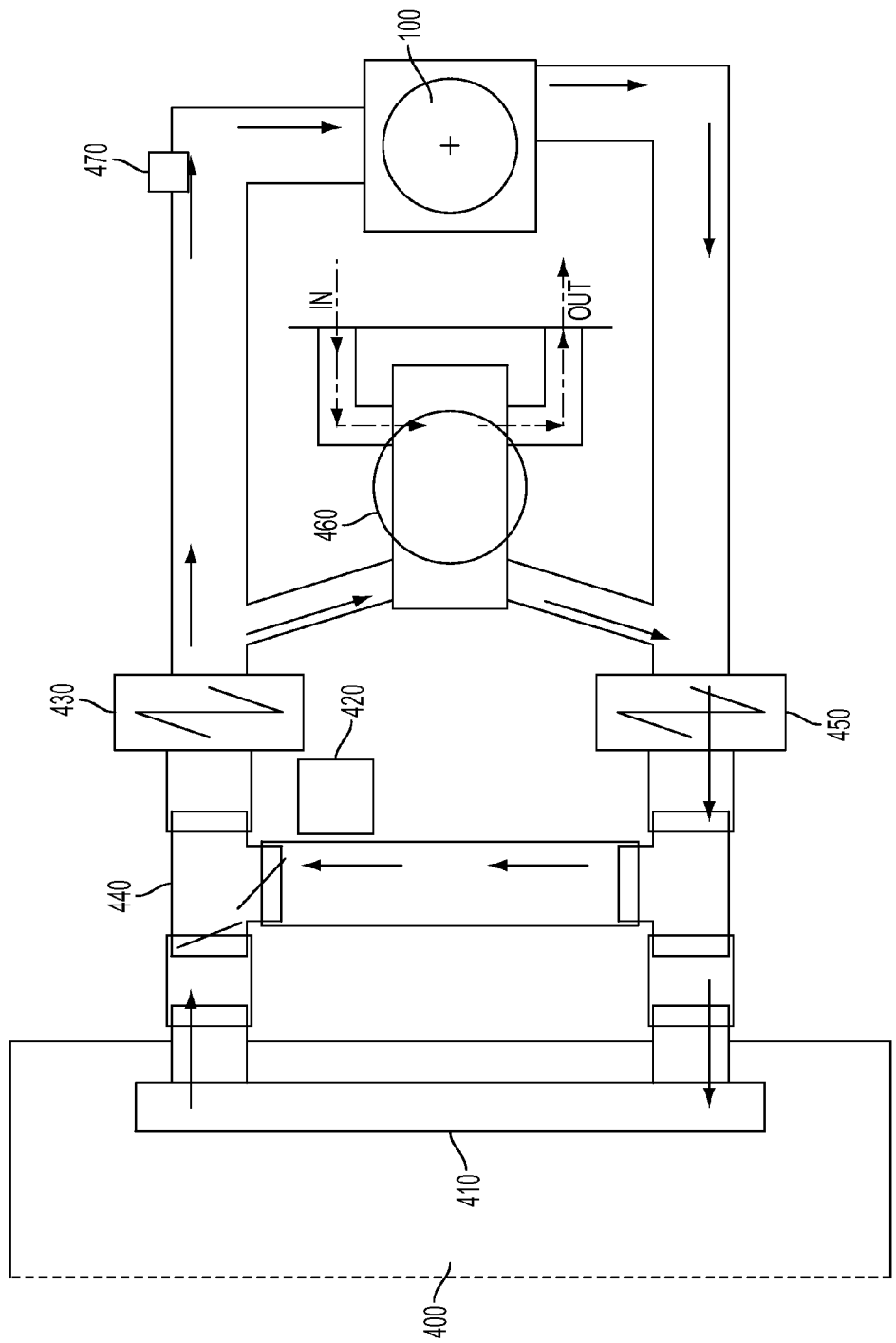

FIG. 4 illustrates the generalized air circulation pattern of the refrigeration system. A LIC (Liquid Injected $CO_2$) box 400 is a component of the refrigeration system of the present invention. Liquid $CO_2$ is injected into the LIC box 400 by means of an internal injection manifold. When the liquid $CO_2$ is injected into the manifold it decompresses and cools as enters the inside of the LIC box 400 through several nozzles and forms "snow." A tubing array 410 passes through the LIC box 400 and acts as a heat exchanger. It then distributes cool air to the fly chambers 100 and returns warmer air that has already been distributed to the fly chambers 100. An air handler controller 420 manages the circulation of the air in and out of the fly chambers 100. The air handler 420 monitors sensors for temperature and humidity in the fly chamber, and operates control valves in the duct system.

In a preferred embodiment, fans 430 are used to continuously move refrigerated air into the fly chambers 100 and return warmer air toward the LIC box 400 the temperature within the fly chambers 100 is kept between 35° F. and 39° F. through the use of a thermocouple in conjunction with an air flow mixing valve 440, located within the circulation tube 410. If the temperature of the air flowing through the circulation tube 410 reaches a temperature below 35° F., the air recirculation flow mixing valve 440 opens and allows warmer return air in and keeps colder air out to raise the air temperature within the circulation tube 410, and thus within the fly chambers 100. The inline variable speed fan 430 is utilized to increase the speed of the airflow in order to increase output of colder air and intake of warmer air. If the temperature of the air flowing through the circulation tube 410 reaches a temperature greater than 39° F., the air recirculation flow mixing valve closes 440 and the inline variable speed fan 450 speeds up to increase the speed of the fly chamber air recycling through the LIC box 400 in order to more rapidly cool a greater amount of air for return to the fly chambers. This fly chamber refrigeration system is also fitted with a dessicant system to maintain any desired humidity level within the fly chambers. The fly chamber refrigeration system may also be fitted with an injection system to allow doping of insects via aromatherapy prior to their release.

It should be noted that refrigeration systems other than a Liquid-Injected-$CO_2$ system as described above can be used without departing from the spirit and scope of the invention. For example, dry ice pellets, nuggets, blocks, snow formed from liquid CO2, etc., may all be used. In many applications, 3 mm compressed dry ice pellets may be particularly effective. A conventional refrigerated freezer system may also be used to chill and maintain a temperature of 0 degrees Fahrenheit or below in the LIC Box 400.

Conversely, the refrigeration system disclosed herein may be used in connection with other applications such as the transportation of temperature-sensitive medical materials, frozen and chilled foods or products, chilled live crustaceans, and other temperature-sensitive products.

Sterile or genetically altered flies are housed within the fly containment cylinders 180 within each fly chamber 100. The fly chambers 100 are inserted and sit above the nesting chutes 170. As the refrigeration system cools the cylinders 180 within each fly chamber 100, the flies become physically retarded and lose their ability to fly and otherwise physically function, causing them to succumb to the force of gravity. Once refrigerated the flies are released from the fly chambers 100. As the aircraft travels at approximately 1,200 feet above ground level, the pilot, operator, or CPU triggers the release of the fly chamber release gates 160 and the physically retarded refrigerated flies drop into the nesting chutes 170 and are released to the exit chute 150 by the spiral release controller 140. The flies then fall to the ground below where they quickly regain normal temperature and function. In an embodiment utilizing a Cessna Caravan approximately 60 million sterile or genetically altered fruit flies are dropped over a desired area. The concentration of flies per square mile can be controlled based upon the speed of the shafts 140 and carrying aircraft.

The CPU system for the fly release machine is linked to the aircraft navigation system to allow release rates to be continuously adjusted to compensate for airspeed variation. The release machine is also linked to its own GPS driven computer control system which permits precise pre-flight designation of target release areas, in-flight verification of release patterns and rates. Post-flight, complete continuous fly release machine operating data including fly chamber temperatures and humidity, release rates and times, and exact release areas may be downloaded.

Figure 5:
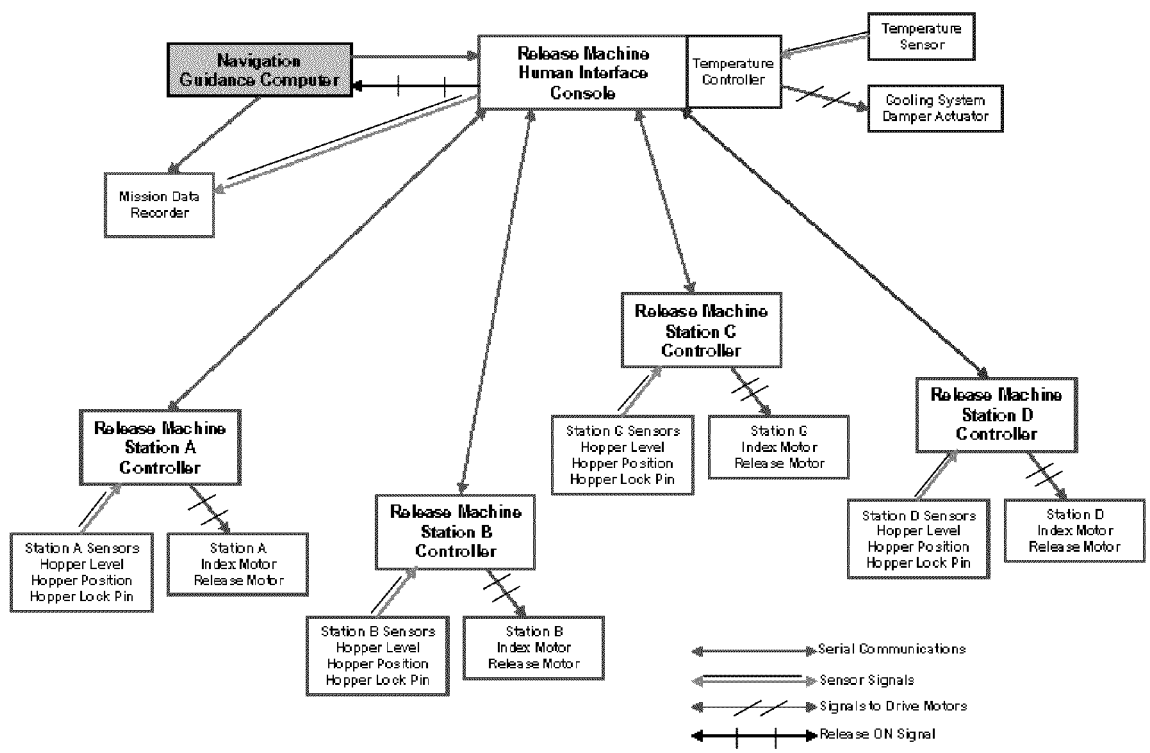

FIG. 5 is a block diagram illustrating the electronic control system in accordance with an embodiment of the invention. The electronic control system of the invention in its preferred embodiment controls the dispensing of insects (or other materials) by using the outputs from commercially available GPS Navigation Guidance Systems. A navigation guidance system is programmed with the desired geographic dispensing areas and dispensing rate. When a geographic area to be treated is entered, a signal is sent to the release machine to start dispensing. The guidance system determines the ground speed of the aircraft (or any type of vehicle). The ground speed value is multiplied by the desired application rate. This value is broadcast, preferably using serial bus communications, to all of the hopper stations. Each hopper station's dispensing motor will turn at a rate to reflect the desired dispensing rate. The dispensing rate is specified in a value of insects (or other material) dispensed per linear mile traveled. Variations of the ground speed would speed up or slow down the dispensing motor to maintain the desired dispensing rate. The hopper stations have individual control units. Each hopper control has programmable dispensing rate scaling. The scaling allows multiple hoppers to have different dispensing rates. Scaling is beneficial when different species of insects are to be dispensed during the same mission. For example, a scaling rate of 1 will result in dispensing at the rate programmed into the navigation guidance system, and a scaling rate of 0.5 will result in dispensing at ½ the rate programmed into the navigation guidance system. Each hopper station preferably has a self-contained control system such that, if a malfunction occurs with one, the others will continue to function. The hopper container is designed with multiple chambers. Each hopper control has sensors to determine when a chamber has been emptied. When a chamber is empty the hopper control indexes a motor to rotate the container to the next chamber. Position sensors indicate when the next chamber is in the correct position and stops the index motor. When the last chamber has been emptied, the container is indexed back to the starting position for refilling.

The control scheme is preferably designed as a modular system. In the preferred embodiment, the components of the control system and their functions are as follows.

Human Interface Console

The console receives the pre-programmed mission parameters from the Navigation Guidance System, and then broadcasts the information to the hopper control units. The console also serves as an interface to the hopper control units. The operator has indicator lights to show the hopper container position, which chambers have been emptied, and if the container has become jammed during indexing. The console has a rotary switch for each station. The switch has the function of overriding the mission parameters. The dispensing process can be halted or placed in a manual mode. There are two manual mode dispensing rates that can be chosen. Each is software programmable.

The interface console also preferably includes a commercially available refrigeration system controller and a humidity indicator.

Hopper Dispensing Controllers

The dispensing control receives mission parameters to control dispensing rate, and dispensing on/off. Dispensing on/off is controlled by the Navigation Guidance System and the operator override switch. The controller monitors position and contents of the hopper to control the indexing of the container.

Temperature Controller

Monitors temperature of air circulating through the hopper containers and controls a damper to regulate temperature.

Mission Data Recorder

A digital data recorder is preferably provided for recording mission parameters for verification and quality control purposes. Information that can be recorded includes, but is not limited to: GPS information, latitude, longitude, altitude, actual dispensing rate of each hopper station, air temperature at various points along the refrigeration system airflow, and relative humidity of refrigeration system airflow.

While the invention has been described in detail and with reference to specific embodiments thereof, it will be apparent to those skilled in the art that various changes and modifications can be made therein without departing from the spirit and scope thereof. Thus, it is intended that the present invention cover the modifications and variations of this invention provided they fall within the spirit and the scope of the invention as described herein. One of ordinary skill in the art will recognize that the present invention can be modified to accommodate the dispensing of insects other than fruit flies which are subject to the same susceptibility, or to accommodate dispensing of non-insect means for eradication of pests, without departing from the spirit and scope of the invention. Examples of such means include, e.g., insects, seeds, bait stations, various varmint baits, sterile screw worm flies, and any other biological control. Such means would each benefit from the release control (density per mile or zone), quality control data, and/or release verification by GPS that are provided by the invention. The release machine of the invention may be used to release such means with or without utilizing the chilling and temperature control methods described above.

Furthermore, although the invention in its preferred embodiment as described herein is utilized for aerial release, it will be understood by those skilled in the art that the invention can be utilized for ground-based operations without departing from the spirit and scope of the invention.

The invention claimed is:

1. A system for releasing genetically altered insects into an insect population, the system comprising:
   a base secured to a carrying vehicle;
   a temperature regulation system housed within the carrying vehicle to regulate the temperature of genetically altered insects;
   at least one removable cartridge to hold said genetically altered insects removably attached to the base;
   a release on each at least one removable cartridge allowing genetically altered insects to transfer to a nesting chute proximate each at least one chamber and secured to the base;
   a controllable mechanism between the nesting chute and an exit chute to regulate the amount of genetically altered insects directed into the exit chute, wherein the genetically altered insects travel through the exit chute and are dispensed out of the carrying vehicle.

2. The system of claim 1, wherein the temperature is regulated to be between about 30° to 39° F.

3. The system of claim 1, wherein the temperature is regulated to be about 34° F.

4. The system of claim 1, further comprising a humidity control system.

5. The system of claim 4, wherein the humidity control system regulates the humidity between about 20 to 50 percent relative humidity.

6. The system of claim 4, wherein the humidity control system regulates the humidity at about 25 percent relative humidity.

7. The system of claim 1, further comprising a CPU and a motor for controlling the rotation of the controllable mechanism, wherein the speed of rotation determines the rate of insects dispensed into the exit chute.

8. The system of claim 1, wherein the temperature regulation system further comprises a heat exchanger.

9. The system of claim 8, wherein the heat exchanger comprises a liquid injected $CO_2$ box.

10. The system of claim 1, wherein an exiting end of the exit chute is substantially tapered.

11. A genetically altered insect release apparatus comprising:
   a cabinet comprising:
      an air quality maintenance system; and
      at least one rotatable cartridge;
   the at least one rotatable cartridge having a plurality of spokes radiating outward from a central axis of the cartridge and dividing the cartridge into a plurality of compartments for holding genetically altered insects;
   a member with a closable opening therein between the at least one compartment and a chute, wherein the cartridge rotates to dispense the genetically altered insects from each of the plurality of compartments through the closable opening; and
   a rotatable member that assists the movement of genetically altered insects from the chute to an exit passageway.

12. The genetically altered insect release apparatus of claim 11, wherein the exit passageway terminates in a venturi.

13. The genetically altered insect release apparatus of claim 11, wherein the air quality maintenance system maintains the air at a temperature below about 39° F.

14. The genetically altered insect release apparatus of claim 11, wherein the air quality maintenance system maintains the air at a temperature about 30° F.

15. The genetically altered insect release apparatus of claim 11, wherein the air quality maintenance system maintains the air at a relative humidity above about 20 percent.

16. The genetically altered insect release apparatus of claim 11, wherein the air quality maintenance system maintains the air at a relative humidity below about 50 percent.

17. The genetically altered insect release apparatus of claim 11, further comprising GPS capability, wherein a predetermined amount of insects can be released at a predetermined location.

* * * * *